United States Patent [19]

Müller et al.

[11] Patent Number: 5,691,337

[45] Date of Patent: Nov. 25, 1997

[54] OXY-PHENYL-(PHENYL)GLYCINOLAMIDES WITH HETEROCYCLIC SUBSTITUENTS

[75] Inventors: Ulrich Müller, Wuppertal, Germany; Richard Connell, Trumbull, Conn.; Siegfried Goldmann; Klaus-Helmut Mohrs, both of Wuppertal, Germany; Siegfried Raddatz, Köln, Germany; Michael Matzke, Wuppertal, Germany; Rudi Grützmann, Solingen, Germany; Martin Beuck, Milford, Conn.; Stefan Wohlfeil, Hilden, Germany; Hilmar Bischoff, Wuppertal, Germany; Dirk Denzer, Wuppertal, Germany

[73] Assignee: Bayer Aktiengesellschaft, Leverkusen, Germany

[21] Appl. No.: 785,146

[22] Filed: Jan. 13, 1997

Related U.S. Application Data

[62] Division of Ser. No. 566,460, Dec. 1, 1995.

[30] Foreign Application Priority Data

Dec. 9, 1994 [DE] Germany .................. 44 43 891.5

[51] Int. Cl.$^6$ .................. A61K 31/495; C07D 217/00
[52] U.S. Cl. .................. 514/249; 514/307; 514/422; 514/427; 514/443; 544/353; 544/354; 546/146; 548/525; 548/564; 549/58
[58] Field of Search .................. 514/443, 249, 514/307, 422, 427; 544/353, 354; 549/58; 546/146; 548/525, 564

[56] References Cited

U.S. PATENT DOCUMENTS 4,898,876  2/1990  Fujii et al. .................. 544/391

*Primary Examiner*—Joseph McKane
*Assistant Examiner*—Richard S. Myers, Jr.
*Attorney, Agent, or Firm*—Sprung Kramer Schaefer & Briscoe

[57] ABSTRACT

Oxy-phenyl-(phenyl)glycinolamides with heterocyclic substituents are prepared by reaction of the corresponding oxyphenylcarboxylic acids with heterocyclic substituents with phenylglycinol. The new substances are suitable as active compounds in medicaments, in particular in agents having an antiatherosclerotic action.

5 Claims, No Drawings

OXY-PHENYL-(PHENYL)GLYCINOLAMIDES WITH HETEROCYCLIC SUBSTITUENTS

This application is a divisional of application Ser. No. 08/566,460, filed Dec. 1, 1995, now allowed.

The present invention relates to oxy-phenyl-(phenyl) glycinolamides with heterocyclic substituents, to a process for their preparation and to their use as antiatherosclerotic agents.

It is known that increased blood levels of triglycerides (hypertriglyceridaemia) and cholesterol (hypercholesterolanaemia) are associated with the origin of atherosclerotic changes to the vascular wall and coronary heart diseases.

Furthermore, a significantly increased risk of the development of coronary heart diseases exists if these two risk factors occur in combination, which in turn is accompanied by over-production of apolipoprotein B-100. There is therefore still a goat need to provide active medicaments for combating atherosclerosis and coronary heart diseases.

The compounds, 2(R')- and 2(S')-2-[4-(quinolin-2-yl-methoxy)phenyl]-2-cyclopentylacetic acid (S)-phenylglycinolamide are known from the publication EP-344 519.

The present invention now relates to oxy-phenyl-(phenyl)glycinolamides with heterocyclic substituents, of the general formula (I)

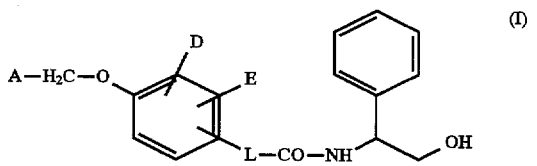

in which

A represents naphthyl, or represents a radical of the formula

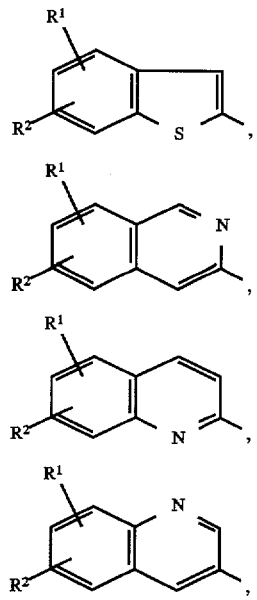

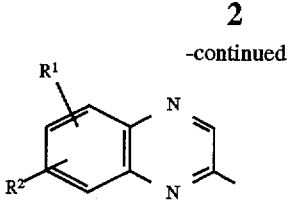

or

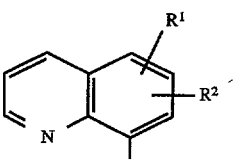

wherein $R^1$ and $R^2$ are identical or different and denote hydrogen, halogen, hydroxyl or straight-chain or branched alkoxy having up to 4 carbon atoms, D and E are identical or different and represent hydrogen, cycloalkyl having 3 to 8 carbon atoms, azido, hydroxyl, halogen, straight-chain or branched alkyl, alkoxy or alkenyl having in each case up to 6 carbon atoms, or a 5- to 6-membered unsaturated or saturated heterocyclic radical having up to 3 hetero atoms from the series consisting of S, N and/or O or represent a radical of the formula —$NR^3R^4$ or —$NR^5SO_2$—$R^6$, wherein $R^3$, $R^4$ and $R^5$ are identical or different and denote hydrogen or straight-chain or branched alkyl having up to 4 carbon atoms, benzyl or phenyl, $R^6$ denotes straight-chain or branched alkyl having up to 4 carbon atoms, benzyl or phenyl, which is optionally substituted by straight-chain or branched alkyl having up to 4 carbon atoms, L represents a bond, or represents a radical of the formula

wherein $R^7$ denotes hydrogen, hydroxyl, methoxy or halogen, $R^8$ denotes hydrogen, hydroxyl, halogen, straight-chain or branched alkenyl or alkoxy having in each case up to 8 carbon atoms or cycloalkyl or cycloalkenyl having in each case 3 to 14 carbon atoms, or denotes straight-chain or branched alkyl having up to 8 carbon atoms, which is optionally substituted by cycloalkyl having 3 to 8 carbon atoms, phenyl or tetrahydropyranyl, which in their turn can be substituted by halogen, or denotes a radical of the formula —$CH_2SiR^9R^{10}R^{11}$ or an indanyl radical, wherein $R^9$, $R^{10}$ and $R^{11}$ are identical or different and denote straight-chain or branched alkyl having up to 4 carbon atoms or $R^7$ and $R^8$ together with the carbon atom form a saturated carbocyclic ring having 5 to 7 carbon atoms, which is optionally substituted up to twice in an identical or different manner by straight-chain or branched alkyl having up to 4 carbon atoms, or $R^7$ and $R^8$ together form a radical of the formula =O or a double bond radical of the formula

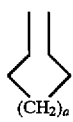

wherein
a denotes the number 2, 3, 4, 5 or 6, and salts thereof, excluding 2(R')- and 2(S')-2-[4-(quinolin-2-yl-methoxy)phenyl]-2-cyclopentylacetic acid (S)-phenylglycinolamide.

The oxy-phenyl-(phenyl)glycinolamides according to the invention with heterocyclic substituents can alto be in the form of their salts. Salts with organic or inorganic bases or acids may be mentioned here in general.

Physiologically acceptable salts are preferred in the context of the present invention. Physiologically acceptable malts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group or a tetrazolyl radical. Particularly preferred salts are, for example, sodium, potassium, magnesium or calcium salts, as well as ammonium salts, which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

A heterocyclic radical is in general a 5- to 6-membered, saturated or unsaturated ring which can contain up to 3 oxygen, sulphur and/or nitrogen atoms as hereto atoms. 5- and 6-membered ring with one oxygen, sulphur and/or up to 2 nitrogen atoms are preferred. Preferred rings which are mentioned are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

A 5- to 6-membered saturated heterocyclic radical which can furthermore contain up to 3 oxygen, sulphur and/or nitrogen atoms as hetero atoms is in general piperidyl, morpholinyl, piperazinyl or pyrrolidinyl. Morpholinyl is preferred.

A carbocyclic radical in general is a 3- to 7-membered, preferably 5- to 7-membered, saturated hydrocarbon ring. Cyclopentyl, cyclohexyl or cycloheptyl are mentioned as preferred.

The compounds according to the invention can exist in stereoisomeric forms which either behave as mirror images (enantiomers) or do not behave as mirror images (diastereomers). The invention relates both to the enantiomers or diastereomers or their particular mixtures. These mixtures of enantiomers and diastereomers can be separated into the stereoisomerically uniform constituents in a known manner.

The following diastereomers of the formulae (Ia) and (Ib) are mentioned as examples:

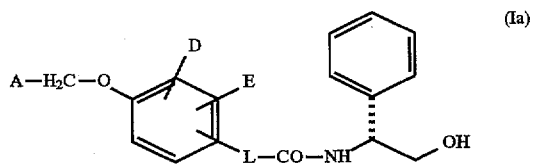

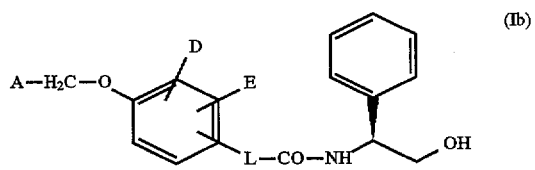

Preferred compounds of the general formula (I) are those in which

A represents naphthyl or represents a radical of the formula

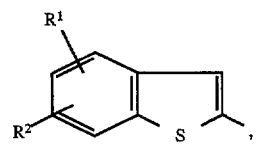

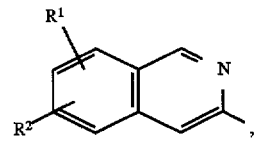

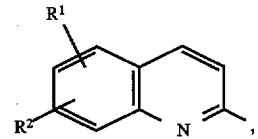

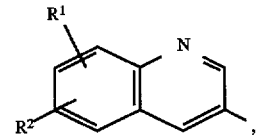

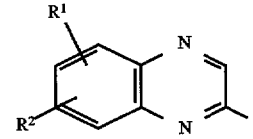

or

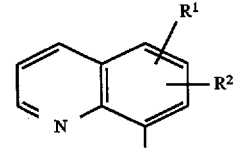

wherein
$R^1$ and $R^2$ are identical or different and denote hydrogen, fluorine, chlorine, bromine, hydroxyl or straight-chain or branched alkoxy having up to 3 carbon atoms, D and E are identical or different and represent hydrogen, cyclopropyl, cyclopentyl, cyclohexyl, azido, hydroxyl, fluorine, chlorine, bromine, straight-chain or branched alkyl, alkoxy or alkenyl having in each case up to 5 carbon atoms, pyrrolyl or imidazolyl, or represent a radical of the formula —NR³R⁴ or —NR⁵—SO₂—R⁶, wherein R³, R⁴ and R⁵ are identical or different and denote hydrogen, straight-chain or branched alkyl having up to 3 carbon atoms or phenyl, R⁶ denotes straight-chain or branched alkyl having up to 3 carbon atoms, benzyl or phenyl, which is optionally substituted by straight-chain or branched alkyl having up to 3 carbon atoms, L represents a bond, or represents a radical of the formula

wherein

R⁷ denotes hydrogen, hydroxyl, methoxy, fluorine, chlorine or bromine,

R⁸ denotes hydrogen, hydroxyl, halogen, straight-chain or branched alkenyl or alkoxy having in each case up to 7 carbon atoms, cyclopentyl, cyclohexyl, cycloheptyl, cyclooctyl, cyclooctyl, cyclodecyl, cycloundecyl, cyclododecyl or cyclohexenyl, or denotes straight-chain or branched allyl having up to 7 carbon atoms, which is optionally substituted by cyclopentyl, cyclohexyl, cycloheptyl, cyclooctyl, phenyl or tetrahydropyranyl, which in their turn can be substituted by fluorine, chlorine or bromine, or denotes a radical of the formula CH₂—SiR⁹R¹⁰R¹¹ or an indanyl radical, wherein R⁹, R¹⁰ and R¹¹ are identical or different and denote straight-chain or branched alkyl having up to 3 carbon atoms, or R¹³ and R¹⁴ together with the carbon atom form a cyclopentyl, cyclohexyl or cycloheptyl ring, which are optionally substituted up to twice by methyl, or R⁷ and R⁸ together form a radical of the formula =O or a double bond radical of the formula

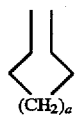

wherein a denotes the number 2, 3 or 4, and salts thereof, excluding 2(R')- and 2(S')-2-[4-(quinolin-2-yl-methoxy)phenyl]-2-cyclopentylacetic acid (S)-phenylglycinolamide.

Particularly preferred compounds of the general formula (I) are those in which

A represents naphthyl or represents a radical of the formula

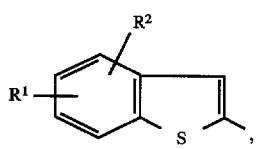

-continued

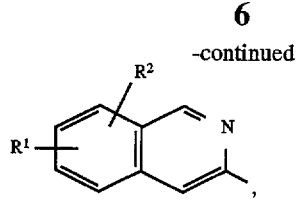

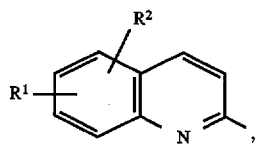

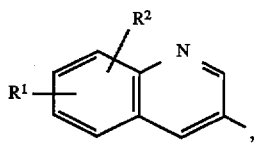

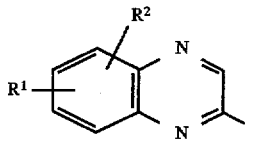

or

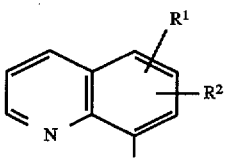

wherein

R¹ and R² are identical or different and denote hydrogen, fluorine, chlorine, bromine, hydroxyl or methoxy, D and E are identical or different and represent hydrogen, cyclopropyl, cyclopentyl, cyclohexyl, azido, hydroxyl, fluorine, chlorine, bromine, straight-chain or branched alkyl, alkoxy or alkenyl having in each case up to 5 carbon atoms, pyrrolyl or imidazolyl, or represent a radical of the fomula —NR⁵—SO₂R⁶, wherein R⁵ denotes hydrogen or methyl, R⁶ denotes straight-chain or branched alkyl having up to 3 carbon atoms, benzyl or phenyl, which is optionally substituted by methyl or ethyl, L represents a bond, or represents a radical of the formula

wherein

R⁷ denotes hydrogen, hydroxyl, fluorine or methoxy,

R⁸ denotes hydrogen, hydroxyl, straight-chain or branched alkenyl or alkoxyl, having in each case up to 6 carbon atoms, cyclopentyl, cyclohexyl, cycloheptyl, cyclooctyl, cyclooctyl, cyclodecyl, cycloundecyl, cyclododecyl or cyclohexenyl, or denotes straight-chain or branched alkyl having up to 6 carbon atoms, which is optionally substituted by cyclopentyl, cyclohexyl, cycloheptyl, phenyl or tetrahydropyranyl, which in their turn can be substituted by fluorine, chlorine or bromine, or denotes a radical of the formula CH₂Si(R⁹R¹⁰R¹¹) or an indanyl radical, wherein $R^9$, $R^{10}$ and $R^{11}$ denote methyl, or $R^7$ and $R^8$ together with the carbon atom form a cyclopentyl, cyclohexyl or cycloheptyl ring, which are optionally substituted up to twice by methyl, or $R^7$ and $R^8$ together denote a radical of the formula =O or a double bond radical of the formula

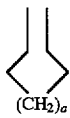

wherein a denotes the number 2, 3 or 4, and salts thereof, excluding 2(R')- and 2(S')-2-[4-(quinolin-2-yl-methoxy)phenyl]-2-cyclopentylacetic acid (S)-phenylglycinolamide.

A process has also been found for the preparation of the compounds of the general formula (I) according to the invention, characterized in that carboxylic acids of the general formula (II)

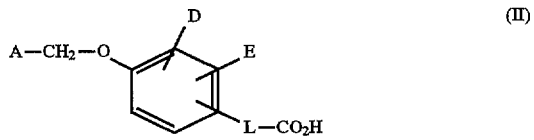

in which

A, D, E and L have the meaning given, if appropriate with prior activation of the carboxylic acid function, are reacted with phenylglycinol of the formula (III)

if appropriate under an inert gas atmosphere, if appropriate in inert solvents, in the presence of a base and/or an auxiliary, and in the case where $R^3$, $R^4$ and/or $R^5 \ne H$, an alkylation follows if appropriate, and if appropriate the substituents $R^1$, $R^2$, D and E are varied.

The process according to the invention can be illustrated by way of example by the following equation:

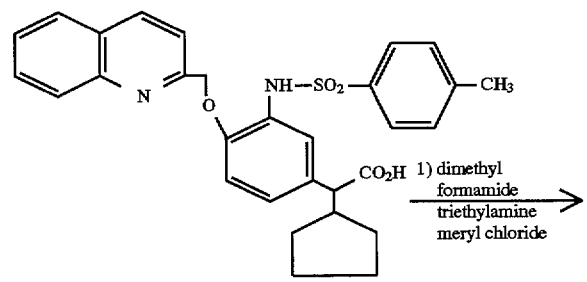

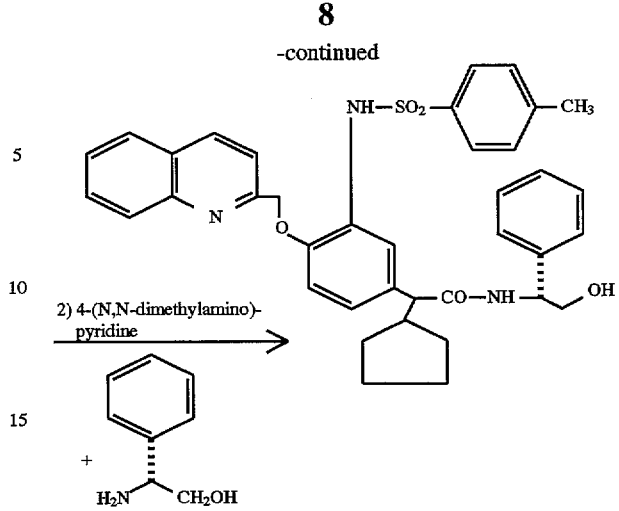

Suitable solvents here are inert organic solvents which do not change under the reaction conditions. These include ethers, such as diethyl ether or tetrahydrofuran, halogenated hydrocarbons, such as methylene chloride, chloroform, carbon tetrachloride, 1,2-dichloroethane, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Methylene chloride, tetrahydrofuran, acetone or dimethylformamide are particularly preferred.

Suitable bases are the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholales, such as, for example, sodium ethanolate or potassium ethanolate or sodium methanolate or potassium methanolate, or organic amines, such as triethylamine, picoline or N-methylpiperidine, or amides, such as sodium arnide or lithium diisopropylamide, or organometallic compounds, such as butyllithium or phenyllithium. Sodium carbonate and potassium carbonate and triethylamine are preferred.

The base is employed in an amount of 0.6 mol to 5 mol, preferably 0.7 mol to 2 mol, per mole of the compound of the general formula (II).

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Compounds which are suitable for activation of the carboxylic acid function are in general bases and/or dehydrating reagents, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphoric acid anhydride or isobutyl chloroformate or benzotriazolyloxy-tris-(dimethylamino)phosphonium hexafluorophosphate or phosphonic acid diphenyl ester-amide or methanesulphonyl chloride, if appropriate in the presence of bases, such as triethylamine or N-ethylmorphotine or N-methylpiperidine or dicyclohexylcarbodiimide and N-hydroxysuccinimide.

The acid-binding agents and dehydrating reagents are in general employed in an amount of 0.5 to 3 mol, preferably 1 to 1.5 mol, per mole of the corresponding carboxylic acids.

The carboxylic acid function is in general activated in a temperature range from 0° C. to 160° C., preferably from 30° C. to 80° C., and if appropriate under an inert gas atmosphere.

The compounds of the general formula (II) are known (cf. EP 582 908, 344 519, 339 416, 399 291, 414 078, 529 450; and 414 076; U.S. Pat. Nos. 4,929,629, 4,970,215, 5,091, 392, 5,126,354, DE 410,555.1, 4,112,533.9, 41,128,681.2, 4,219,765.1, 4,226,519.3, 4,226,649.1), or they can be prepared by a process in which compounds of the general formula (IV)

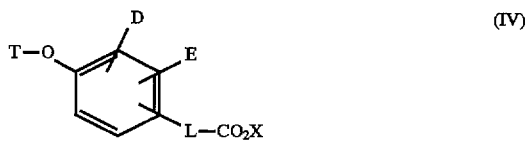

(IV)

in which

D, E and L have the meaning given,

T represents a typical hydroxy-protective group, preferably benzyl or tert-butyl, and X represents hydrogen or represents $(C_1-C_4)$-alkyl, after this protective goup has been split off by customary methods, are reacted with compounds of the general formula (V)

$A-CH_2Z$ (V)

in which

A has the abovementioned meaning and

Z represents halogen, preferably bromine, in inert solvents, if appropriate in the presence of a base, and in the case of the acids, the esters are hydrolysed.

The compound of the general formula (III) is known.

The compounds of the general formula (IV) and (V) are known per se or can be prepared by customary methods.

The compounds of the general formula (I) according to the invention have an unforeseeable pharmacological action spectrum.

The known compounds 2(R')- and 2(S')-2-[4-(quinolin-2-yl-methoxy)phenyl]-2-cyclopentylacetic acid (S)-phenylglycinolamide also show this new pharmacological action spectrum, in addition to their lipoxygenase-inhibiting action.

They can be used as active compounds in medicaments for reducing changes to vascular walls and for treatment of coronary heart diseases, cardiac insufficiency, disturbances in cerebral performance, ischaemic cerebral diseases, apoplexy, circulatory disturbances, disturbances in microcirculation and thromboses.

Furthermore, proliferation of smooth muscle cells plays a decisive role in the occlusion of vessels. The compounds according to the invention are capable of inhibiting this proliferation and therefore of preventing atherosclerotic processes.

The compounds according to the invention are distinguished by a reduction in ApoB-100-associated lipoproteins (VLDL and its breakdown products, such as LDL), ApoB-100, triglycerides and cholesterol. They therefore have valuable pharmacological properties which are superior compared with the prior art.

Surprisingly, the action of the compounds according to the invention initially comprises a reduction or complete inhibition of the formation and/or release of ApoB-100-associated lipoproteins from liver cells, which results in a reduction in the plasma VLDL level. This reduction in VLDL must be accompanied by a reduction in the plasma levels of ApoB-100, LDL, triglycerides and cholesterol; several of the abovementioned risk factors which participate in changes to the vascular wall are thus reduced at the same time.

The compounds according to the invention can therefore be employed for prevention and treatment of atherosclerosis, obesity, pancreatitis and constipation.

1. Inhibition of the release of ApoB-100-associated lipoproteins

The test for detection of the inhibition of the release of ApoB-100-associated lipoproteins from liver cells was carried out in vitro with cultured liver cells, preferably with cells of the human line HepG2. These cells are grown under standard conditions in a medium for culture of eukaryotic cells, preferably in RPMI 1640 with 10% fetal calf serum. HepG2 cells synthesize and secrete into the culture supernatant ApoB-100-associated lipoprotein particles, which in principle are built up similarly to the VLDL and LDL particles which are to be found in plasma.

These particles can be detected with an immunoassay for human LDL. This immunoassay is carried out with antibodies which have been induced against human LDL under standard conditions in the rabbit. The anti-LDL antibodies (rabi-anti-LDL-ab) were purified by affinity chromatogaphy on an immunosorbent with human LDL. These purified-rab-anti-LDL-ab are adsorbed onto the surface of plastic. This adsorption is expediently effected on the plastic surface of microlitre plates with 96 wells, preferably on MaxiSorp plates (Nunc). If ApoB-100-associated paaicles are present in the soupernatant of Hep-G2 cells, these can bond to the insolubilized rab-anti-LDL-ab, and an immune complex bonded to the plastic surface is formed. Non-bonded proteins are removed by washing. The immune complex on the plastic surface is detected with monoclonal antibodies, which had been induced against human LDL under sandard conditions and purified. These antibodies were conjugated with the enzyme peroxidase (Boehringer, Mannheim). Peroxide conveys the colourless substrate TMB (Kirkegaard and Perry) into a coloured product in the presence of $H_2O_2$. After acidification of the reaction mixture with $H_2SO_4$, the specific lift absorption at 450 nm, which is a measure of the amount of ApoB-100-associated particles which had been secreted into the culture supernatant by HepG2 cells, is determined.

Surprisingly, the compounds according to the invention inhibit the release of the ApoB-100-associated particles. The $IC_{50}$ value indicates the concentration of substance at which the absorption of light is inhibited by 50% in comparison with the control (solvent control without substance).

2) Investigation of the inhibition of the proliferation of smooth muscle cells

The antiproliferative action of the compounds is determined using smooth muscle cells obtained from the aortas of rats by the media explant technique [R. Ross, J. Cell. Biol. 50, 172, 1971]. The cells are sown in suitable culture dishes, as a rule 96-well plates, and cultured for 2–3 days in medium 199 with 7.5% of FCS and 7.5% of NCS, 2 mM L-glutamine and 15 mM HEPES, pH 7.4, in 5% $CO_2$ at 37° C. Thereafter, the cells are synchronized by withdrawal of serum for 2–3 days and then stimulated to growth with serum or other factors. Test compounds are added at the same time. After 16–20 hours, 1 μCi of $^3$H-thymidine is added, and after a further 4 hours the incorporation of this substance into the DNA of the cells which can be precipitated with TCA is determined. For determination of the $IC_{50}$ values, the concentration of active compound is calculated which, on sequential dilution of the active compound, causes half the maximum inhibition of the thymidine incorporation caused by 10% of FCS.

3) Determination of VLDL secretion in vivo (hamster)

The effect of the test substances on VLDL secretion in vivo is investigated on the hamster. For this purpose, golden hamsters are premedicated with atropine (83 mg/kg s.c.) and anaesthetized with Ketavet (83 mg/kg s.c.) and Nembutal (50 mg/kg i.p.). When the animals have become free from reflexes, the *v. jugularis* is exposed and a cannula inserted. 0.25 ml/kg of a 20% strength solution of Triton WR-1339 in physiological saline solution is then administered. This detergent inhibits the lipoprotein lipase and thus leads to an increase in the trigyceride level because of an absence of catabolism of secreated VLDL particles. This increase in triglycerides can be used as a measure of the rate of VLDL secretion. Blood is taken from the animals by puncture of the retroorbital venus plexus before and one and two hours after administration the detergent. The blood is incubated at room temperature for two hours and then at 4° C. overnight in order to conclude coagulation completely. Thereafter, it is centrifuged at 10,000 g for 5 minutes. The triglyceride concentration in the serum thus obtained is determined with the aid of a modified comercially obtainable enzyme test (Merckotest® Triglycerides No. 14354). 100 µl of test reagent are added to 100 µl of serum in 96-well plates and the mixtures are incubated at room temperature for 10 minutes. The optical density is then determined at a wavelength of 492 nm in an automatic plate reader (SLT-Spectra). Serum samples having too high a triglyceride concentration are diluted with physiological saline solution. The triglyceride concentration contained in the samples is determined with the aid of a standard curve measured in parallel. In this model, test substances are administered either intravenously immediately before administration of the detergent or orally or subcutaneously before initiation of the anaesthesia.

4) Inhibition of intestinal tryglyceride absorbtion in vivo (rat)

The substances which are to be investigated for their triglyceride absorption-inhibiting action in vivo are administered orally to male Wistar rats having a body weight of between 170 and 230 g. For this purpose, the animals are divided into groups of 6 animals 18 hours before administration of the substance and their food is then withdrawn. Drinking water is available to the animals ad libitum. The animals of the control group are given an aqueous tragacanth suspension or a tragacanth suspension which contains olive oil. The tragacanth-olive oil suspension is prepared with an Ultra-Turrax. The substances to be investigated are suspended in a corresponding tragacanth-olive oil suspension, likewise with an Ultra-Turrax, directly before administration of the substance.

Before application of the stomach tube, blood is taken from each rat by puncture of the retroorbital venus plexus for determination of the basal serum triglyceride content. The tragacanth suspension, the tragacanth-olive oil suspensions without a substance (control animals) or the substances suspended in a corresponding tragacanth-olive oil suspension, are then administered to the fasting animals with a stomach tube. Further withdrawals of blood for determination of the postprandial increase in serum triglycerides are made as a rule 1, 2 or 3 hours after application via the stomach tube.

The blood samples are centrifuged, and, after the serum has been isolated, the triglycerides are determined photometrically with an EPOS analyser 5060 (Eppenford Gergatebau, Netheler & Hinz GmbH, Hamburg). The triglycerides are determined completely enzymatically with a commercially available UV test.

The postprandial increase in serum triglycerides is determined by subtracting the triglyceride initial value of each animal from its corresponding postprandial triglyceride concentrations (1, 2 and 3 hours after administration).

The differences (in mmol/l) at each point in time (1, 2 and 3 hours) are averaged in the groups and the means of the increase in serum triglycerides ($\Delta TG$) of the animals treated with the substance are compared with those of the animals which received only the tragacanth-oil suspension.

The course of the serum triglyceride of the control animals which were given only tragacanth is also calculated. The effect of the substance at each point in time (1, 2 or 3 hours) is determined as follows and stated in $\Delta\%$ of the oil-loaded control.

$$\Delta \% \text{ increase in triglycerides} = \frac{\Delta TG_{substance} - \Delta TG_{tragacanth\,control}}{\Delta TG_{oil\,loading} - \Delta TG_{tragacanth\,control}} \times 100$$

Effect of 10 mg of test substance/kg of body weight p.o. on the increase in triglycerides ($\Delta\%$) 2 hours after triglyceride loading in the serum of fasting rats. The increase in serum triglyceride of fat-loaded control animals based on the serum triglyceride level of tragacanth control animals corresponds to 100%. n=6 animals per group.

Statistical analysis is by the Student t-test after first checking the variances for homogeneity.

Substances which statistically significantly ($p<0.05$) reduce the postprandial increase in serum triglycerides at a point in time by at least 30% compared with the untreated control group are re prded as pharmacologically active.

5) Inhibition of VDVL secretion in vivo (rat)

The action of the test substances on VLDL secretion is also investigated in the rat. For this, 500 mk/kg of body weight (2.5 mg/kg of Triton WR-1339 dissolved in physiological saline solution are administered intravenously into the tail vein of rats. Triton WR-1339 inhibits the lipoprotein lipase and thus leads to an increase in the triglyceride and cholesterol level by inhibition of VLDL catabolism. These increases can be used as a measure of the rate of VLDL secretion.

Blood is taken from the animals by puncture of the retroorbital venous plexus both before and one and two hours after administration of the detergent. The blood is incubated at room temperature for 1 hour for coagulation and the serum is isolated by centrifugation at 10 000 g for 20 seconds. The triglycerides are then determined photometrically at a wavelength of 540 nm by means of a commercially available coupled enzyme test (Sigman Diagnostics®, No. 339). The measurement is made at a wavelength of 546 nm with the aid of an enzyme test which is likewise coupled (Boehringer Mannheim®, No. 1442350). Samples with triglyceride or cholesterol concentrations which exceed the measurement range of the methods are diluted with physiological saline solution. The particular serum concentrations are determined with the aid of standard series measured in parallel. Test substances are administered orally, intravenously or subcutaneously immediately after the Triton injection.

The invention also relates to a combination of oxyphenyl (phenyl) glycerol amides containing heterocyclic substituents of the general formula (I) with a glucosidase and/or amylase inhibitor for the treatment of formula hyperlipidemia, obesity (adipositas) and diabetes mellitus. Glucosidase and/or amylase inhibitors in the context of the invention are for example Acarbose, Adiposine, Voglibose (AO-128), Miglitol, Emiglitate, MDL-25637, Camiglibose (MDL-73945), Tendamistate, A1-3688, Treslatin, Pradimicin-Q and Salboslatin. A combination of Acarbose, Miglitol, Emiglitate or Voglibose with one of the abovementioned compounds of the general formula (I) is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, i.e. in amounts which are sufficient to achieve the stated dosage range.

The formulations are prepared, for example, by extending the active compounds with solvents and/or excipients, if appropriate using emulsifying agents and/or dispersing agents, and in the case of the use of water as a diluent, for example, organic solvents can be used as auxiliary solvents if appropriate.

Administration is carried out in the customary manner, preferably orally or parenterally, in particular perlingually or intravenously.

In the case of parenteral use, solutions of the active compound can be employed, using suitable liquid carrier materials.

In general, it has proved advantageous in the case of intravenous administration to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

Nevertheless, it may be necessary to deviate from the amounts mentioned, and in particular to do so as a function of the body weight or type of administration route, of the behaviour of the individual towards the medicament, the nature of its formulation and the time or interval at which administration takes place. Thus, in some cases it may be sufficient to use less than the abovementioned minimum amount, while in other cases the upper limit mentioned must be exceeded. In the event of administration of relatively large amounts, it may be advisable to divide these into several individual doses over the day.

Solvent mixtures used:

| A | Δ | petroleum ether:acetone | = 1:1 |
| B | Δ | petroleum ether:ethyl acetate | = 1:1 |
| C | Δ | methylene chloride:methanol | = 10:1 |
| D | Δ | methylene chloride:ethyl acetate | = 1:1 |
| E | Δ | methylene chloride:methanol | = 20:1 |
| F | Δ | methylene chloride:ethanol | = 50:1 |
| G | Δ | methylene chloride:methanol | = 50:1 |
| H | Δ | methylene chloride:ethyl acetate | = 5:1 |

Abbreviations used:

| Ac = | acetyl |
| Bn = | benzyl |
| Bz = | benzoyl |
| iBu = | iso-butyl |
| nBu = | normal butyl |
| sBu = | secondary butyl |
| tBu = | tertiary butyl |
| cDec = | cyclo-decyl |
| DMF = | N,N-dimethylformamide |
| DMSO = | dimethyl sulphoxide |
| cDodec = | cyclo-dodecyl |
| Et = | ethyl |
| cHept = | cyclo-heptyl |
| cHex = | cyclo-hexyl |
| HOBT = | 1-hydroxy-H-benzotriazole |
| Me = | methyl |
| Mes = | mesyl |
| cNon = | cyclo-nonyl |
| cOct = | cyclo-octyl |
| cPent = | cyclo-pentyl |
| nPent = | normal pentyl |
| Ph = | phenyl |
| cPr = | cyclo-propyl |
| nPr = | normal propyl |
| iPr = | iso-propyl |
| THF = | tetrahydrofuran |
| TMS = | tetramethylsilane |
| pTol = | para-tolyl |
| pTos = | para-tosyl |
| cUndec = | cyclo-undecyl |

Definition of the isomer types:

| 4dia = | mixture of the four possible diastereomers with two centres of asymmetry in the molecule |
| dia A = | diastereomer having the higher $R_f$ value |
| dia B = | diastereomer having the lower $R_f$ value |
| ent = | enantiomer |
| 2 ent dia = | mixture of two enantiomerically pure diastereomers |
| ent dia A = | enantiomerically pure diastereomer having the higher $R_f$ value |
| ent dia B = | enantiomerically pure diastereomer having the lower $R_f$ value |
| R = | R enantiomer |
| rac = | racemate |
| rac dia A = | racemic diastereomer having the higher $R_f$ value |
| rac dia B = | racemic diastereomer having the lower $R_f$ value |
| S = | S enantiomer |

STARTING COMPOUNDS

Example I

Cyclononanol

25.3 g of cyclononanone are dissolved in 200 ml of anhydrous ether and reacted with 10.25 g of lithium alanate at room temperature. After 1.5 hours, the mixture is hydrolysed carefully with an aqueous sodium chloride solution and then extracted with ether/aqueous citric acid. The organic phase is dried with magnesium sulphate and evaporated in vacuo.

Yield: 25.6 g $R_f$=0.26 (methylene chloride) characteristic $^1$H-NMR signal (CDCl$_3$, 250 MHz, TMS): δ=3.88 (m, 1H, CH—OH) ppm.

Example II

Cycloundecanol

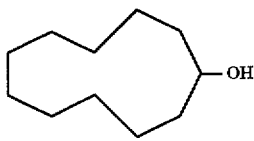

9.6 g of cycloundecanone are reacted analogously to the instructions for Example I.

Yield: 9.3 g R$_f$=0.28 (methylene chloride) characteristic $^1$H-NMR signal (CDCl$_3$, 250 MHz, TMS): δ=3.88 (m, 1H, CH—OH).

Example III

Cyclononyl bromide

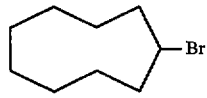

5.0 g of the compound from Example I are stirred with 12 ml of 48% strength hydrobromic acid and 2.8 ml of concentrated sulphuric acid at room temperature for 6 hours. Methylene chloride is then added and the organic phase is washed several times with water until the aqueous phase, after extraction by shaking has a pH>5. The methylene chloride solution is dried with magnesium sulphate and evaporated in vacuo. According to $^1$H-NMR, the crude product thus obtained contains no starting material, although Z-cyclononene is found in the crude product.

Total yield: 5.1 g molecular ratio of cyclononyl bromide: Z-cyclononene=8.8:1 characteristic $^1$H-NMR signals (CDCl$_3$, 250 MHz, TMS): cyclononyl bromide: δ=4.41 ppm (m, 1H, CHBr) Z-cyclononene: δ=5.53 ppm (m, 2H, CH=CH)

Example IV

Cycloundecyl bromide

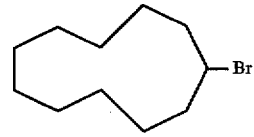

The reaction is carried out with 2.6 g of the compound from Example II analogously to the instructions for Example III.

Yield: 2.5 g of crude product characteristic $^1$H-NMR signal (CDCl$_3$, 250 MHz, TMS): δ=4.36 ppm (m, 1H, CHBr).

The crude cycloundecyl bromide is further reacted with the olefinic by products of E- and Z-olefin.

Example V

Methyl 2-[4-(quinolin-2-yl-methoxy)phenyl]-2-cyclononyl-acetate

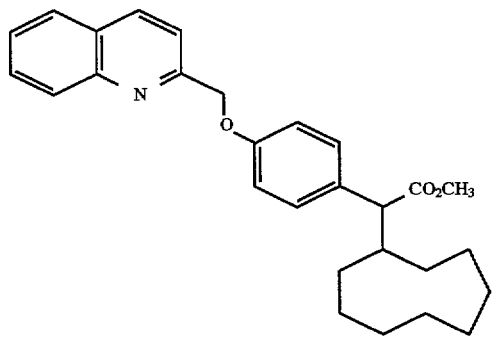

7.11 g of methyl 2-[4-(quinolin-2-yl-methoxy)phenyl] acetate (U.S. Pat. No. 4,970,215) in 50 ml of anhydrous DMF at 0° C. are stirred with 3.23 g of potassium tert-butanolate in 40 ml of anhydrous DMF, the mixture is subsequently stirred at 0° C. for 1 hour and 5.1 g of the compound from Example III are then added. The mixture is subsequently stirred for a total of 20 hours, while warming gradually to room temperature, and is poured onto water and ether and brought to pH≈4 with 2M hydrochloric acid. The organic phase is separated off, dried with magnesium sulphate and evaporated. The crude product thus obtained is purified by column-chromatography (silica gel 60, Merck 40–63 μm, petroleum ether:ethyl acetate=10:1). In addition to re-isolated starting material, 2.8 g of product are obtained.

R$_f$=0.48 (petroleum ether:ethyl acetate=1:1)

Example VI

Methyl 2-[4-(Quinolin-2-yl-methoxy)phenyl]-2-cycloundecyl-acetate

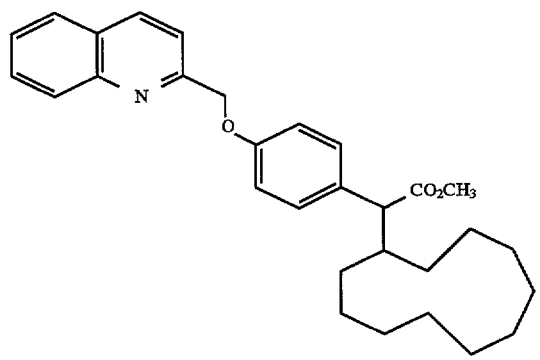

The reaction is carried out with 2.5 g of the compound from Example IV and 3.06 g of methyl 2-[4-(quinolin-2-yl-methoxy)phenyl]acetate (U.S. Pat. No. 4,970,215) analogously to the instructions for Example V.

Yield: 0.72 g R$_f$=0.41 (petroleum ether:ethyl acetate=5:1)

Example VII

2-[4-(Quinolin-2-yl-methoxy)phenyl]-2-cyclononyl-acetic acid

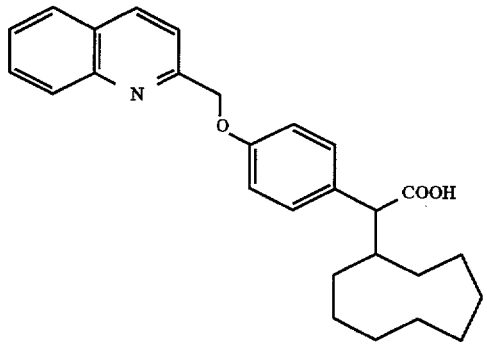

2.06 g of the compound from Example V are boiled under reflux in 40 ml of ethanol with 20 ml of 2M aqueous sodium hydroxide solution for 10 hours. The cooled reaction mixture is poured into ether/water, and the alkaline aqueous phase is brought to pH≈2 with 1M hydrochloric acid and extracted again with ether. The organic phase mentioned last is dried with magnesium sulphate and evaporated to dryness in vacuo.

Yield: 0.3 g $R_f$=0.04 (petroleum ether:ethyl acetate=5:1)

Example VIII

2-[4-(Quinolin-2-yl-methoxy)phenyl]-2-cycloundecyl-acetic acid

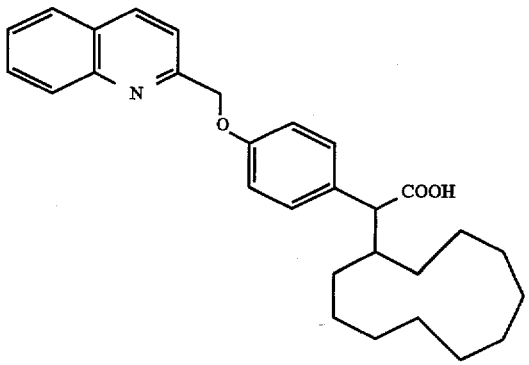

The reaction is carried out with 0.5 g of the compound from Example VI analogously to the reaction instructions of Example VII.

Yield: 0.46 g $R_f$=0.37 (methylene chloride:methanol=20:1)

Example IX

Methyl 2-[3-(Amino-4-(quinolin-2-yl-methoxy)phenyl]-2-cyclopentylacetate

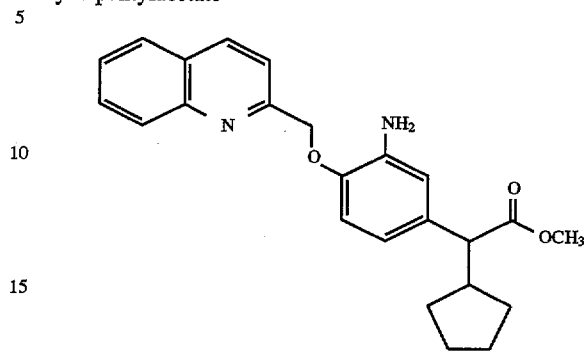

1 g of methyl 2-[3-(nitro-4-(quinolin-2-yl-methoxy) phenyl]-2-cyclopentyl-acetate (2.4 mmol; from DE 41 05 551) is dissolved in THF (5 ml) and methanol (20 ml). Triethylamine (0.486 g, 4.8 mmol) and 1,3-dimercaptopropane (0.52 g 4.8 mmol) are added dropwise. After 18 hours, 1M aqueous HCl (20 ml) is added to the reaction mixture. The solution is evaporated on a rotary evaporator and the residue is dissolved in diethyl ether and water. The aqueous phase is neutralized with NaHCO$_3$ and extracted with diethyl ether (3 times). The diethyl ether phase is dried and evaporated on a rotary evaporator.

Yield: 0.75 g (80%) $R_f$=0.31 (100:2=CH$_2$Cl$_2$:CH$_3$OH) MS (DCI, NH$_3$): 391 ([M+H]$^+$) IR (film): $\tilde{v}$=3434, 3312, 2951, 1735, 1518 cm$^{-1}$

Example X

Methyl 2-[3-(N-mesyl)amino-4-(quinolin-2-yl-methoxy) phenyl]-2-cyclopentyl-acetate

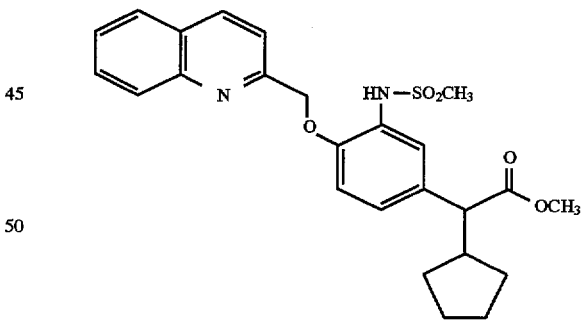

1.2 g of the compound from Example IX (3.0 mmol) are dissolved in 12 ml of CH$_2$Cl$_2$ and the solution is cooled to 0° C. 0.45 g of methanesulphonyl chloride (4.0 mmol) in 4 ml of CH$_2$Cl$_2$ is added dropwise. After 10 minutes, triethylamine (0.37 g, 3.7 mmol) is added and the mixture is warmed to 25° C. After 3 hours, a further 15 ml of CH$_2$Cl$_2$ are added and the solution is washed with 1M aqueous HCl and with saturated aqueous NaHCO$_3$ solution. The solution is dried (Na$_2$SO$_4$) and evaporated on a rotary evaporator. The residue is separated by column chromatography.

Yield: 1.22 g (85%) $R_f$=0.47 (100:2=CH$_2$Cl$_2$:CH$_3$OH)

Example XI

Methyl 2-(3-pyrrolyl-4-(quinolin-2yl-methoxy)phenyl]-2-cyclopentylacetate

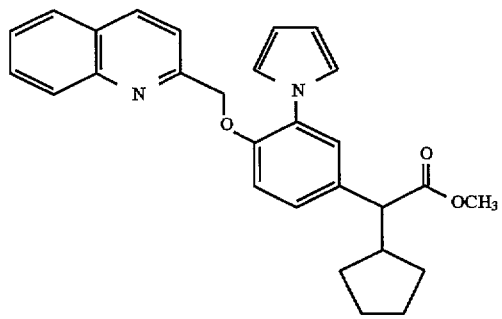

1.0 g of the compound from Example IX (2.56 mmol) is dissolved in 15 ml of acetic acid, 0.42 g of 2,5-dimethoxytetrahydrofuran (3.2 mmol) is added and the mixture is heated at the boiling point for 3 hours. After the acetic acid has been distilled off in vacuo, the residue has been taken up in $CH_2Cl_2$ and the mixture has been extracted by shaking with water, dried ($Na_2SO_4$) and concentrated in vacuo, the residue is separated by column chromatography.

Yield: 0.62 g (55%) $R_f$=0.69 (100:2=$CH_2Cl_2$:$CH_3OH$)
MS (EI): 440 (M$^+$)

Example XII

Methyl 2-[3-(N-tosyl)amino-4-(quinolin-2-yl-methoxy)phenyl]-2-cyclopentylacetate

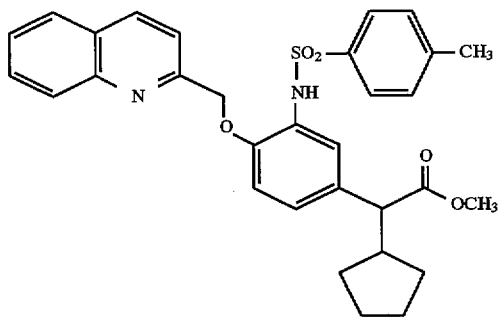

1.2 g of the compound from Example IX (3.1 mmol) are dissolved in 15 ml of $CH_2Cl_2$ and the solution is cooled to 0° C. 0.76 g of p-toluenesulphonyl chloride (4.0 mmol) in 4 ml of $CH_2Cl_2$ is then added dropwise. After 10 minutes, 0.37 g of triethylamine (3.7 mmol) is added and the mixture is warmed to 25° C. After 2 hours, a further 15 ml of $CH_2Cl_2$ are added and the solution is washed with 1M aqueous HCl and with saturated aqueous $NaHCO_3$ solution. The solution is dried ($Na_2SO_4$) and evaporated on a rotary evaporator. The residue is purified by column chromatography.

Yield: 1.07 g (64%) $R_f$=0.27 (100:2=$CH_2Cl_2$:$CH_3OH$)
MS (FAB): 545 (M+H)

Example XIII

2-[3-(N-Mesyl)amino-4-(quinolin-2-yl-methoxy)phenyl]-2-cyclopentylacetic acid

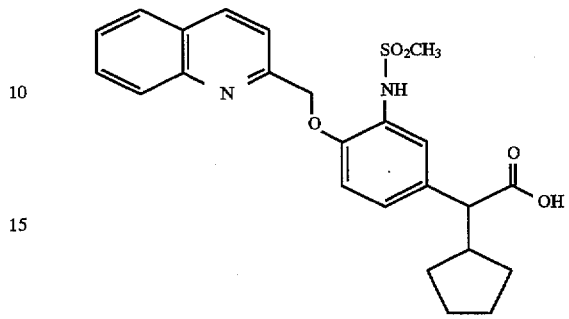

1.14 g of the compound from Example X (2.4 mmol) are dissolved in methanol (10 ml), and 2M sodium hydroxide solution (2.43 ml) is added. After 18 hours, the solution is neutralized with 1M aqueous HCl and then evaporated on a rotary evaporator. The residue is dissolved in 15 ml of $CH_2Cl_2$ and the solution is washed with water. It is dried ($Na_2SO_4$) and evaporated on a rotary evaporator. The residue is separated by column chromatography.

Yield: 0.66 g (60%) $R_f$=0.36 (100:5=$CH_2Cl_2$:$CH_3OH$)

Example XIV

2-[3-Pyrryl-4-(quinolin-2-yl-methoxy)phenyl]-2-cyclopentylacetic acid

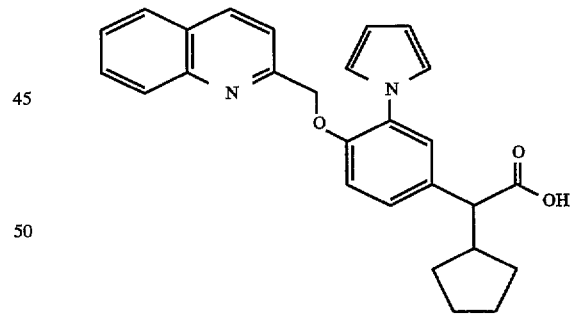

0.57 g of the compound from Example XI (1.3 mmol) is dissolved in methanol (6 ml), and 2M sodium hydroxide solution (1.3 ml) is added. After 18 hours, the solution is neutralized with 1M aqueous HCl and evaporated on a rotary evaporator. The residue is dissolved in 15 ml of $CH_2Cl_2$ and the solution is washed with water. It is dried ($Na_2SO_4$) and evaporated on a rotary evaporator. The residue is separated by column chromatography.

Yield: 0.48 g (85%) $R_f$=0.36 (100:5=$CH_2Cl_2$:$CH_3OH$)

Example XV

2-[3-(N-Tosyl)-amino-4-(quinolin-2-yl-methoxy)phenyl]-2-cyclopentylacetic acid

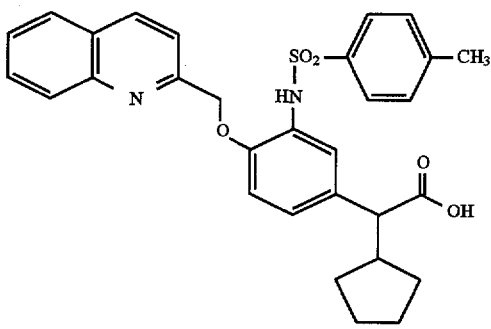

0.99 g of the compound from Example XII (1.8 mmol) is dissolved in methanol (10 ml), and 2M sodium hydroxide solution (7.3 ml) is added. After 18 hours, the solution is neutralized with 1M aqueous HCl and evaporated on a rotary evaporator. The residue is dissolved in 15 ml of $CH_2Cl_2$ and the solution is washed with water. It is dried ($Na_2SO_4$) and evaporated on a rotary evaporator. The residue is separated by column chromatography.

Yield: 0.90 g (94%) $R_f$=0.27 (100:5=$CH_2Cl_2$:$CH_3OH$) m.p. =117° C.

Example XVI 1,1-Dimethoxy-1-(2-fluoro-4-methoxyphenyl)-2-iodoethane

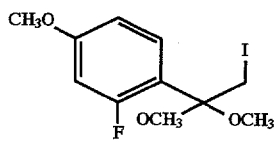

1.68 g of 2-fluoro-4-methoxyacetopheone, 5.3 g of trimethyl orthoformate and 3.0 g of iodine are mixed at room temperature. After 18 hours, a 10% strength aqueous $Na_2S_2O_3$ a solution is added and the mixture is extracted with ethyl acetate. The organic phase is dried ($Na_2SO_4$) and evaporated on a rotary evaporator. The residue is separated by column chromatography.

Yield: 1.7 g (86%) $R_f$=0.6 (1:5=petroleum ether:$CH_2Cl_2$) MS (FAB): 340 ($M^+$), 309, 199

Example XVII

Methyl 2-(2-fluoro-4-methoxyphenyl)-acetate

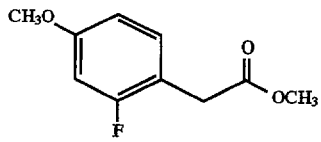

8.9 g of the compound from Example XVI and 27.7 g of trimethyl orthoformate are dissolved in 26 ml of methanol. 5.0 g of silver tetrafluoroborate are added, with exclusion of light. After 14 hours, the solution is diluted with water and diethyl ether. The phases are separated and the organic solution is dried ($Na_2SO_4$) and evaporated on a rotary evaporator. The residue is separated by column chromatography.

Yield: 5.0 g (96%) $R_f$=0.3 (10:1=petroleum ether:ethyl acetate) MS (FAB): 340 ($M^+$) 309, 199

Example XVIII

Methyl 2-(2-fluoro-4-methoxyphenyl)-2-cycloheptylacetate

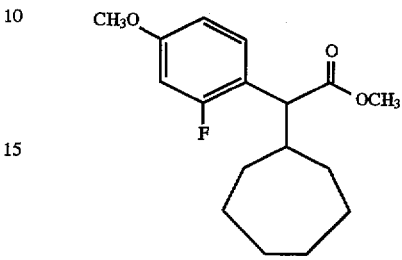

1.5 g of NaH (60% strength in paraffin) are dissolved in 20 ml of DMF and the solution is cooled to 0° C. 5 g of the compound from Example XVII and 5.4 g of cycloheptyl bromide in 20 ml of DMF are added dropwise. The solution is warmed to 25° C. and diluted with water and ethyl acetate. The phases are separated and the solution is washed with water, dried ($Na_2SO_4$) and evaporated on a rotary evaporator. The residue is separated by column chromatography.

Yield: 5.3 g (71%) $R_f$=0.5 (10:1=petroleum ether:ethyl acetate) MS (DCI, $NH_3$): 312 ($M^+$+$NH_3$), 295 ($M^+$), 212, 198, 139

Example XIX

Ethyl 2-(2-fluoro-4-hydroxyphenyl)-2-cycloheptyl acetate

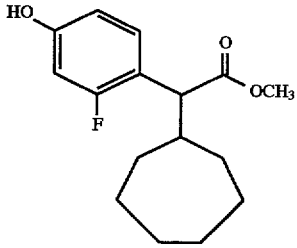

4 g of the compound from Example XVIII are dissolved in 20 ml of $CH_2Cl_2$. The solution is cooled to −78° C. and 100 ml of boron tribromide are added. The solution is warmed to −30° C. and after one hour, to 0° C. After one hour, the solution is cooled to −30° C. and 120 ml of methanol are added. The solution is diluted with water and ethyl acetate. The phases are separated and the organic solution is dried ($Na_2SO_4$) and evaporated on a rotary evaporator. The residue is separated by column chromatography.

Yield: 4.0 g (100%) $R_f$=0.25 (10:1=$CH_2Cl_2$:ethyl acetate)

Example XX

Methyl 2-[2-fluoro-4-(quinolin-2-yl-methyloxy)phenyl]-2-cycloheptylacerate

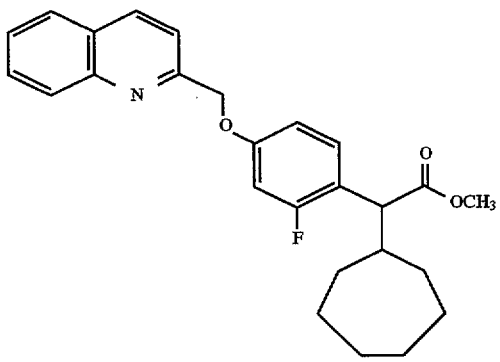

4.0 g of the compound from Example XIX are dissolved in 40 ml of DMF and the solution is added dropwise to 0.68 g of sodium hydride (60% strength in paraffin) in 8 ml of DMF. After 30 minutes, 2.8 g of 2-chloromethyl quinoline in 28 ml of DMF are added dropwise. The solution is warmed to 25° C. and diluted with water and ethyl acetate. The phases are separated and the organic solution is washed with water, dried ($Na_2SO_4$) and evaporated on a rotary evaporator. The residue is separated by column chromatography.

Yield: 5.0 g (87%) $R_f$=0.66 (petroleum ether:ethyl acetate 3:1) MS (FAB): 422 ($M^+$)

Example XXI

2-[2-Fluoro-4-(quinolin-2-yl-methoxy)phenyl]-2-cycloheptylacetic acid

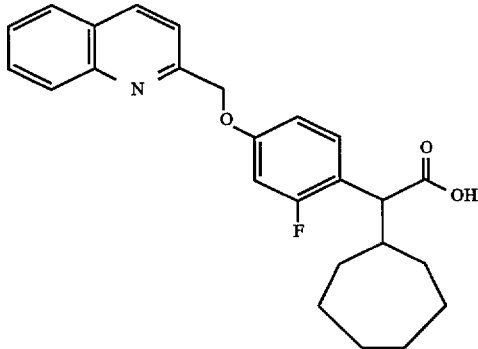

5.0 g of the compound from Example XX are dissolved in 30 ml of methanol, and 17.8 ml of 2M NaOH are added. After 18 hours, the solution is neutralized with 1M HCl. The solution is evaporated on a rotary evaporator and the residue is diluted with water and $CH_2Cl_2$. The phases are separated and the organic solution is dried ($Na_2SO_4$) and evaporated on a rotary evaporator. The residue is separated by column chromatography.

Yield: 4.6 g (95%) $R_f$=0.10 (100:2=$CH_2Cl_2$:$CH_3OH$) MS (DCI, $NH_3$): 408 ($M^+$), 143

Example XXII

Ethyl 2-(3,5-dimethyl-4hydroxyphenyl)-2-oxoacetate

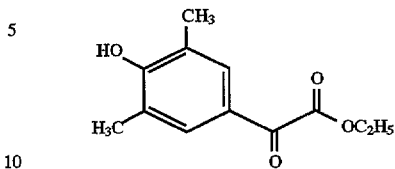

2,6-Dimethylphenyl (2 g) is dissolved in methylene chloride, and ethyl chlorooxalate (2.36 g) is added. 4.27 g of aluminium chloride are added in portions at 10° to 20° C. and the solution is heated to room temperature. After 18 hours, the solution is poured onto ice and extracted with methylene chloride. The organic phase is dried (sodium sulphate) and concentrated and the residue is chromatographed (silica gel 60, Merck, toluene:ethyl=4:1).

Yield: 83% m.p.=113° C. $R_f$=0.52 (ethyl acetate:toluene= 1:4)

Example XXIII

Ethyl 2-[3,5-dimethyl-4-(quinolin-2-yl-methoxy)phenyl]-2-oxo-acetate

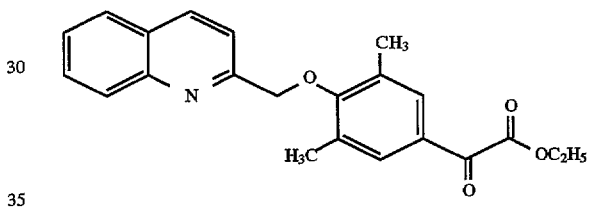

The compound from Example No. XXII is reacted analogously to the instructions of Example No. XX.

Yield: 63% m.p.=72° C. $R_f$=0.40 (ethyl acetate:toluene= 1:9)

Example XXIV

Ethyl 2-[3,5-dimethyl-4-(quinolin-2-yl-methoxy)phenyl]-2-hydroxy-2-cycloheptyl-acetate

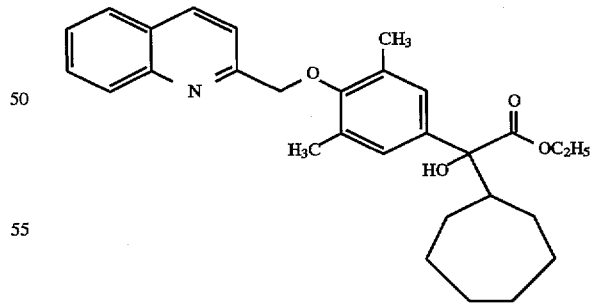

Magnesium (0.4 g) is initially introduced into diethyl ether, and 2.94 g of cycloheptyl bromide are added. The reaction mixture boils, and is boiled further under reflux-(1 hour). The solution is cooled to 0° C. and added dropwise to a solution of ethyl 2-[3,5-dimethyl-4-(quinolin-2-yl-methoxy)phenyl]-2-oxo-acetate (3 g) in tetrahydrofuran (20 ml). After the mixture has been subsequently stirred for 18 hours, the solution is poured into ice-water and extracted with ethyl acetate. The organic phase is dried (Na₂SO₄) and chromatographed (silica gel 60, Merck, methylene chloride-:ethyl acetate:acetic acid=100:5:1).

Yield: 600 mg (16%) R$_f$=0.60 (methylene chloride:ethyl acetate:acetic acid=100:5:1)

Example XXV

2-[3,5-Dimethyl-4-(quinolin-2-yl-methoxy)phenyl]-2-hydroxy)-2-cycloheprylacetic acid

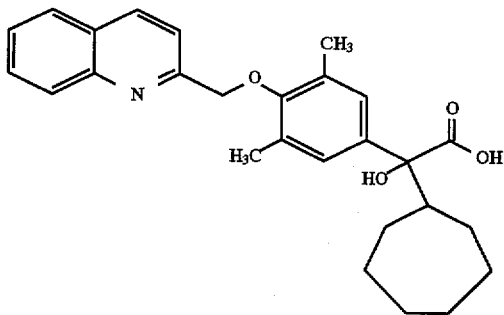

The compound from Example XXIV is reacted analogously to the instructions of Example XXI.

Yield: 76% m.p.=171° C. R$_f$=0.60 (toluene:ethyl acetate:acetic acid=8:2:1)

PREPARATION EXAMPLES

Example 1 and Example 2

2-(S)- and 2-(R)-2-{4-[(quinolin-2-yl)methoxy]phenyl}-2-cyclopentyl-acetic acid (R)-phenyl glycinolamide

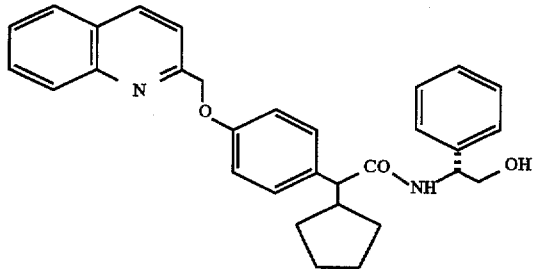

2.5 g (6.9 mmol) of racemic 2-{4-[(quinolin-2-yl)methoxy]phenyl}-2-cyclopentyl-acetic acid (synthesis: U.S. Pat. No. 4,970,215) are dissolved in 25 ml of anhydrous N,N-dimethylformamide, 2.88 ml (20.8 mmol) of triethylamine and 604.7 µl (7.6 mmol) of mesyl chloride are added and the mixture is subsequently stirred at 60° C. for 30 minutes under argon as an inert gas. Thereafter, 1.14 g (8.3 mmol) of (R)-phenylglycinol (commercially obtainable from Aldrich) and 0.84 g (6.9 mmol) of 4-(N,N-dimethylamino)-pyridine, dissolved in 20 ml of anhydrous N,N-dimethylformamide, are added and the mixture is subsequently stirred for a total of 16 hours, while warming slowly to room temperature. Ethyl acetate and water are added to the reaction mixture and the aqueous phase is brought to a pH of about 2 with 1M hydrochloric acid. The organic phase is extracted several times with dilute hydrochloric acid (pH≈2), washed with water and then extracted several times with 0.1M aqueous sodium hydroxide solution. The organic phase is again washed with water, subsequently dried with anhydrous magnesium sulphate and evaporated. Column chromatography (silica gel 60, Merck, 40–63 µm, mobile phase:petroleum ether:ethyl acetate of 5:1 to 1:1) is carried out to separate the components.

Example 1:

R$_f$=0.12 (methylene chloride:ethyl acetate=5:1) Yield: 1.1 g

Example 2:

R$_f$=0.08 (methylene chloride:ethyl acetate=5:1) Yield: 1.0 g

The absolute configuration of the enantiomerically pure carboxylic acids (starting material from Example 1 and 2) is known (EP 509 359), so that the absolute configuration of the products (Example 1 and 2) can be deduced therefrom. The 1H-NMR. spectra of the two diastereomeric products (200 MHz, d6-DMSO, TMS for Example 1/250 MHz, d6-DMSO, TMS for Example 2) show significant differences in the aromatic range:

The H signals of the phenyl radical of the phenylglycinolamide from Example 1 occur in 2 groups (integration: 2H and 3H at about 7.1 and 7.3 ppm); in the case of Example 2, one group (integration: 5H) lies at about 7.3 ppm. This finding can be applied 16 many derivatives of this type.

Example 3 and Example 4

2-[3-Pyrrolyl-4-(quinolin-2-yl-methoxy)phenyl]-2-cyclopentylacetic acid (R)-phenylglycinolamide

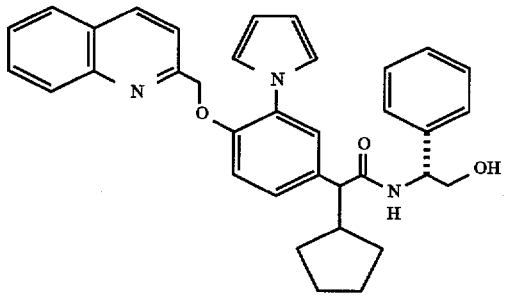

0.445 g of the compound from Example XIV (1.04 mmol), 0.143 g of (R)-phenylglycinol (1.04 mmol) and 0.155 g of 1-hydroxy-1-benzotriazole×H₂O are dissolved in 10 ml of CH₂Cl₂. The solution is cooled to 0° C. and 0.23 g of N'-(3-dimethylaminopropyl)-N-ethylcarbodiimide hydrochloride (1.2 mmol) is added in portions. After 5 minutes, 0.21 g of triethylamine (2.08 mmol) is added dropwise and the solution is warmed to 25° C. A further 15 ml of CH₂Cl₂ are added and the solution is washed with aqueous NH₄Cl and NaHCO₃ solution and with water. The solution is dried (Na₂SO₄) and evaporated on a rotary evaporator. The residue is separated by column chromatography. 0.27 g (49% of theory of a 1:1 mixture of the diastereomers) is obtained. Further separation is carried out by preparative HPLC (250 mm Kromasil 100 C-18, 65% CH₃CN in water).

Example 3:

R$_f$=0.36 (100:5=CH₂Cl₂:CH₃OH) MS (FAB): 546 (M⁺)

Example 4:

R$_f$=0.31 (100:5=CH₂Cl₂:CH₃OH) MS (FAB): 546 (M⁺)

Example 5

2-[2-Fluoro-4-(quinolin-2-yl-methoxy)phenyl]-2-cycloheptylacetic acid (R)-phenylglycinolamide

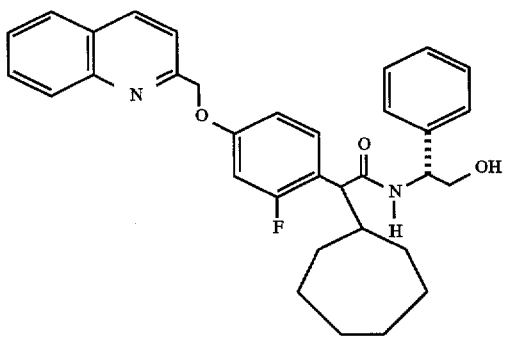

4.6 g of the compound from Example XXI, 1.6 g of (R)-phenylglycinol and 1.7 g of 1-hydroxy-1-benzotriazole×H$_2$O are dissolved in 100 ml of CH$_2$Cl$_2$. The solution is cooled to 0° C. and 2.5 g of N-(3-dimethylaminopropyl)-N-ethylcarbodiimide hydrochloride are added in portions. After five minutes, 2.3 g of triethylamine are added dropwise and the solution is allowed to warm to 25° C. Further CH$_2$Cl$_2$ is added and the solution is washed with NH$_4$Cl and NaHCO$_3$ solution and with waterer. The solution is dried with Na$_2$SO$_4$ and evaporated on a rotary evaporator. The residue is separated by column chromatography.

Yield: 4.9 g (82%, 1:1 diastereomer mixture) R$_f$=0.77 (10:1=CH$_2$Cl$_2$:CH$_3$OH) melting point=167°–168° C.

The compounds in Tables 1 to 7 can be prepared analogously to the instructions of Examples 1 and 2:

TABLE 1

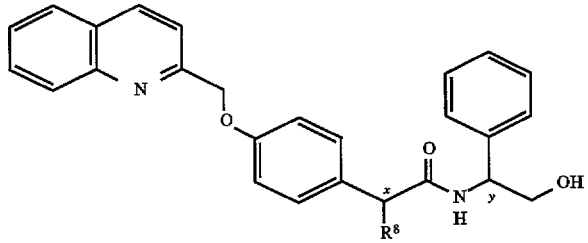

| Ex. No. | x | y | R$^8$ | R$_f$ (solvent) | M.p. [°C.] | Starting compound* (carboxylic acid) |
|---|---|---|---|---|---|---|
| 6 | — | R | H | — | >260 | 1) |
| 7 | rac | R | Me | 0.33/0.20 (D) | | 1) |
| 8 | rac | R | Et | 0.29 (E) | | 1) |
| 9 | rac | R | nPr | 0.29 (E) | | 1) |
| 10 | rac | R | iPr | 0.15 (E) | | 1) |
| 11 | rac | R | nBu | 0.51 (D) | | 1) |
| 12 | rac | R | sBu(rac) | 0.45 (E) | | 1) |
| 13 | rac | R | iBu | 0.46 (E) | | 1) |
| 14 | rac | R | E-CH$_3$CH=CHCH$_2$ | 0.31 (E) | | 1) |
| 15 | rac | R | CH$_3$(CH$_2$)$_4$ | 0.31 (E) | | 1) |
| 16 | rac | R | (C$_2$H$_5$)$_2$CH | 0.55 (C) | | 1) |
| 17 | rac | R | (CH$_3$)$_2$C=CHCH$_2$ | 0.27 (E) | | 1) |
| 18 | rac | R | (CH$_3$)$_2$C=CH(CH$_2$)$_2$ | 0.49 (F) | | 1) |
| 19 | rac | R | OMe | 0.26/0.13 (D) | | 1) |
| 20 | dia A | S | Me | | 156–159 | 2) |
| 21 | dia B | S | Me | | 144–146 | 2) |
| 22 | S | S | cPent | 0.12 (H) | | 2) |
| 23 | R | S | cPent | 0.08 (H) | | 2) |
| 24 | rac | R | cHex | 0.52/0.59 (C) | | 2) |
| 25 | S | R | cHex | 0.52 (D) | | 2) |
| 26 | R | R | cHex | 0.59 (D) | | 2) |
| 27 | S | R | cHept | | 176 | 2) |
| 28 | R | S | cHept | | 160–162 | 2) |
| 29 | S | S | cHept | | 192–194 | 2) |
| 30 | R | R | cHept | | 191–193 | 2) |
| 31 | rac | R | cOct | 0.14/0.09 (F) | | 3) |
| 32 | S | R | cOct | 0.14 (F) | | 3) |
| 33 | R | R | cOct | 0.09 (F) | | 3) |
| 34 | rac | R | cNon | 0.54/0.44 (E) | | Ex. VII |
| 35 | S | R | cNon | 0.44 (E) | | Ex. VII |
| 36 | R | R | cNon | 0.54 (E) | | Ex. VII |
| 37 | rac | R | cDec | 0.29/0.39 (E) | | 3) |
| 38 | S | R | cDec | 0.29 (E) | | 3) |
| 39 | R | R | cDec | 0.39 (E) | | 3) |
| 40 | rac | R | cUndec | 0.33/0.44 (E) | | Ex. No. VIII |
| 41 | rac | R | cDodec | 0.20/0.11 (G) | | 3) |
| 42 | rac | R | cPent-CH$_2$ | 0.36 (E) | | 2) |

TABLE 1-continued

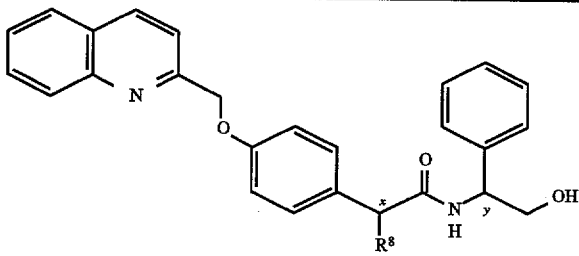

| Ex. No. | x | y | R⁸ | $R_f$ (solvent) | M.p. [°C.] | Starting compound* (carboxylic acid) |
|---|---|---|---|---|---|---|
| 43 | rac | R | cHex-CH₂ | 0.69 (C) | | 2) |
| 44 | rac | R | CH₂-C₆H₄-F | 0.62 (C) | | |
| 45 | rac | R | CH₂-(tetrahydropyran-2-yl) | 0.46 (C) | | |

1) US 4 929 629
2) US 4 970 215
3) US 5 091 392

TABLE 2

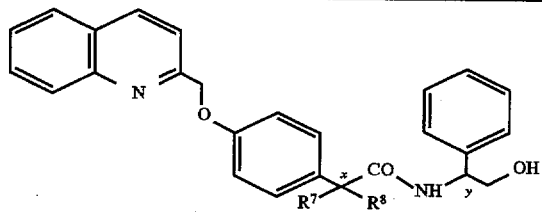

| Ex. No. | x | y | R⁷ | R⁸ | $R_f$ (solvent) | M.p. [°C.] | Starting compound* (carboxylic acid) |
|---|---|---|---|---|---|---|---|
| 46 | rac | R | OH | Et | 0.55/0.57 (C) | | |
| 47 | rac | R | OH | nBu | 0.39/0.46 (C) | | |
| 48 | rac | R | OH | iBu | 0.31 (E) | | |
| 49 | rac | R | OH | cPent | 0.39 (E) | | |
| 50 | rac | R | OH | cHex | 0.47 (C) | | 4) |
| 51 | dia A | R | OH | cHex | 0.47 (C) | | 4) |
| 52 | dia B | R | OH | cHex | 0.47 (C) | | 4) |
| 53 | dia A | R | OH | cHept | | 215–217 | 5) |
| 54 | dia B | R | OH | cHept | | 162–164 | 5) |
| 55 | dia A | S | OH | cHept | | 226 | |
| 56 | dia B | S | OH | cHept | | 164–166 | 5) |
| 57 | rac | R | OH | indanyl | 0.54 (C) | | 6) |

TABLE 2-continued

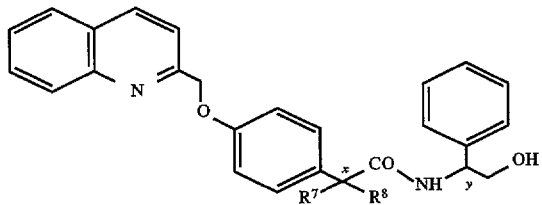

| Ex. No. | x | y | R⁷ | R⁸ | $R_f$ (solvent) | M.p. [°C.] | Starting compound* (carboxylic acid) |
|---|---|---|---|---|---|---|---|
| 58 | rac | R | OCH₃ | cHept | 0.61/0.45 (E) | | |
| 59 | dia A | R | OCH₃ | cHept | 0.61 (E) | | |
| 60 | dia B | R | OCH₃ | cHept | 0.45 (E) | | |
| 61 | rac | R | F | cHept | 0.49/0.58 (E) | | |

EP 414 078
5) US 5 126 154
6) EP 529 450

TABLE 3

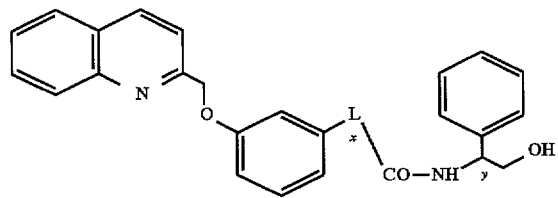

| Ex. No. | x | y | L | $R_f$ (solvent) |
|---|---|---|---|---|
| 62 | / | R | single bond | 0.27 (D) |
| 63 | / | R | —CH₂— | 0.42 (C) |
| 64 | rac | R | cyclopentyl | 0.61 (D) |
| 65 | rac | R | CH₂CH₂CH₂CH₃ isobutyl | 0.51 (D) |
| 66 | rac | R | cycloheptyl-isopropyl | 0.74 (D) |
| 67 | rac | R | cycloheptyl-OH | 0.52 (D) |

TABLE 4

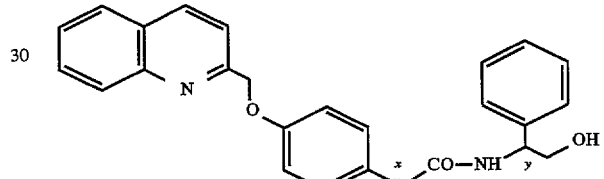

| Ex. No. | x | y | L | $R_f$ (solvent) | Starting compound (carboxylic acid) |
|---|---|---|---|---|---|
| 68 | / | R | single bond | 0.49 (C) | |
| 69 | / | R | cyclopentyl | 0.67 (C) | 7) |
| 70 | / | R | cycloheptylidene | 0.31 (B) | 7) |
| 71 | / | R | cyclohexyl | 0.36 (E) | 7) |

7) EP 414 076

TABLE 5
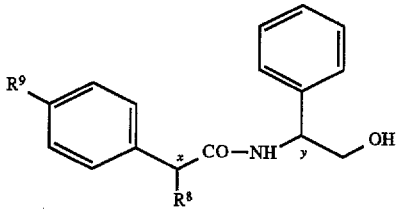
| Ex. No. | x | y | R⁹ | R⁸ | $R_f$ (solvent) | M.p. [°C.] |
|---|---|---|---|---|---|---|
| 72 | rac | R | 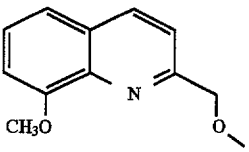 | cPent | | 182–183 |
| 73 | rac | R | 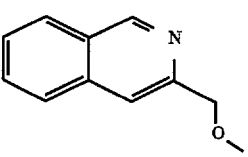 | cPent | 0.50 (A) | |
| 74 | rac | R | 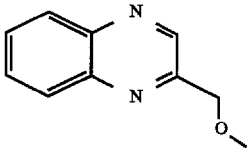 | cPent | | 156–159 |
| 75 | rac | R | 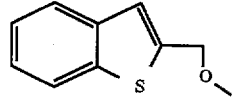 | cPent | | 163–164 |
| 76 | rac | R | 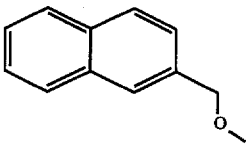 | cPent | | 163 |
| 77 | rac | R | 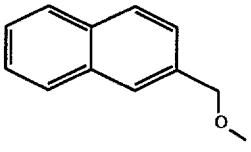 | cHept | 0.62/0.71 (C) | |
| 78 | rac | R | 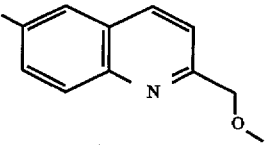 | cPent | | 179–181 |
| 79 | rac | R | 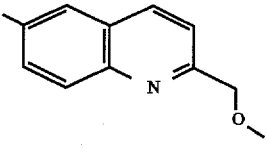 | cPent | | 183–185 |

TABLE 5-continued

Structure: R⁹-substituted phenyl-CH(R⁸)-CO-NH-CH(phenyl)-CH₂-OH (with x and y stereocenters)

| Ex. No. | x | y | R⁹ | R⁸ | $R_f$ (solvent) | M.p. [°C.] |
|---|---|---|---|---|---|---|
| 80 | rac | R | 6-F, 8-F quinolin-2-yl-CH₂-O- | cPent | | 198–200 |

TABLE 6

Structure: R¹-substituted quinolin-2-yl-CH₂-O-phenyl(D)-CH(R⁸)-CO-NH-CH(phenyl)-CH₂-OH

| Ex. No. | x | y | R¹ | D | R⁸ | $R_f$ (solvent) | M.p. [°C.] | M.S. FAB | Starting compound |
|---|---|---|---|---|---|---|---|---|---|
| 81 | R/S | R | H | m-OCH₃ | cHept | 0.27 (E) | | 538 | DE 4 105 551 |
| 82 | R/S | R | H | m-F | cHept | 0.30 (E) | | 526 | DE 4 105 551 |
| 83 | R/S | R | H | m-Cl | cHept | 0.20 (E) | | 543 | DE 4 105 551 |
| 84 | R/S | R | H | (m)-NH-Mes | cPent | 0.20 (E) | | 574 (M⁺) | Ex. No. XIII |
| 85 | R/S | R | H | (m)-NHpTos | cPent | 0.32 (E) | | 650 (M⁺) | Ex. XV |
| 86 | R/S | R | H | cPr | cPent | 0.46 (E) | 145–153 | 521 | DE 4 105 551 |
| 87 | R/S | R | H | (m)-i-Bu | cPent | 0.42 (E) | 174–178 | 537 | DE 4 105 551 |
| 88 | R/S | R | H | (m)-Et | cPent | 0.49 (E) | 170–180 | | DE 4 105 551 |
| 89 | R/S | R | H | (m)-Cl | cPent | 0.51 (E) | 175–185 | | DE 4 105 551 |
| 90 | R | R | H | (m)-F | cPent | 0.41 (E) | 148–153 | 499 | DE 4 105 551 |
| 91 | S | R | H | (m)-N₃ | cPent | 0.72 (C) | 187–189 | | DE 4 105 551 |
| 92 | R/S | R | H | (m)-N₃ | cPent | 0.72 (C) | 165–166 | | DE 4 105 551 |
| 93 | R/S | R | H | (m)-CH₂CH=CH₂ | cPent | 0.77 (C) | | | DE 4 105 551 |
| 94 | R/S | R | H | (m)-E-CH=CHCH₃ | cPent | 0.77 (C) | | 521 | DE 4 105 551 |
| 95 | R/S | R | H | (o)-Br | cPent | 0.64 (E) | | | EP 582 908 |
| 96 | R/S | R | H | (o)-nPr | cPent | 0.56 (E) | 157 | 523 | EP 582 908 |
| 97 | R/S | R | H | m-Br | cPent | 0.81 (C) | | | DE 4 105 551 |
| 98 | R/S | R | H | m-OCH₃ | cPent | 0.81 (E) | | | DE 4 105 551 |
| 99 | R/S | R | H | m,m'-Me₂ | cHept | 0.29 (E) | | 553 | Ex. No. XXV |

The compounds of the following Table 7 are prepared analogously to the instructions of Example 1 and 2:

TABLE 7

| Ex. No. | x | y | R⁸ | M.p. [°C.] |
|---|---|---|---|---|
| 100 | rac | S | nBu | 138 |
| 101 | rac | S | cPent | 134–138 |
| 102 | rac | S | cHex | 145–150 |
| 103 | rac | S | cHept | 127–129 |

The compounds following Table 8 are prepared analogously to the instructions of Example 1 and 2:

TABLE 8

| Ex. No. | x | y | R¹ | R⁸ | M.p. [°C.] |
|---|---|---|---|---|---|
| 104 | rac | S | 6-F | cHept | 161–167 |
| 105 | rac | S | 6-Br | cPent | 172–176 |
| 106 | rac | S | 6-F | cPent | 189–193 |
| 107 | rac | S | 7-Cl | cPent | 202 |

The compounds of the following Table 9 are prepared analogously to the instructions of Example 1 and 2:

TABLE 9

| Ex. No. | x | y | \L/ | M.p. [°C.] |
|---|---|---|---|---|
| 108 | | S | CH₂ | >260 |
| 109 | | S | (4,4-dimethylcyclohexyl) | 146–147 |

TABLE 9-continued

| Ex. No. | x | y | \L/ | M.p. [°C.] |
|---|---|---|---|---|
| 110 | rac | S | CH(OMe) | 156–161 |
| 111 | rac | S | CH(cHex) | 167–169 |
| 112 | rac | S | CH(cyclohexenyl) | 165–168 |
| 113 | | S | (1,1-cyclopentyl) | 159–161 |
| 114 | | S | C=O | 174–176 |

TABLE 10

| Ex. No. | x | y | R⁷ | R⁸ | M.p. [°C.] |
|---|---|---|---|---|---|
| 115 | rac | S | H | (CH₃)₂C=CHCH₂ | 150–153 |
| 116 | rac | S | H | cPrCH₂ | 162–164 |
| 117 | rac | S | H | Et | 180–182 |
| 118 | rac | S | H | CH₂SiMe₃ | 130–133 |
| 119 | rac | S | H | nBu | 140–143 |
| 120 | rac | S | H | cHexCH₂ | 177–181 |

The compounds of the following Table 11 are prepared analogously to the instructions of Example 1 and 2:

TABLE 11

| Ex. No. | x | y | D | R⁸ | M.p. [°C.] |
|---|---|---|---|---|---|
| 121 | dia A | S | H | cPent | 168 |
| 122 | dia B | S | H | cPent | 153 |
| 123 | rac | S | H | cPent | 158–162 |
| 124 | dia B | S | H | cHex | 171 |
| 125 | dia A | S | H | cHex | 223 |
| 126 | dia A | S | m-iBu | cPent | 151 |
| 127 | dia A | S | m-iBu | cHept | 183 |
| 128 | dia B | S | m-iBu | cHept | 183 |

We claim:

1. Oxy-phenyl-(phenyl)glycinolamides with heterocyclic substituents, of formula (I)

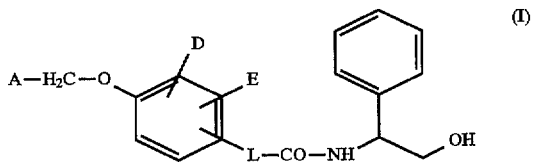

in which

A represents naphthyl, or represents a group of the formula

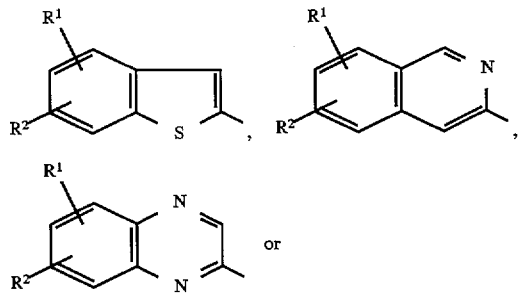

wherein

R¹ and R² are identical or different and denote hydrogen, halogen, hydroxyl or straight-chain or branched alkoxy having up to 4 carbon atoms, D and E are identical or different and represent hydrogen, cycloalkyl having 3 to 8 carbon atoms, azido, hydroxyl, halogen, straight-chain or branched alkyl, alkoxy or alkenyl having in each case up to 6 carbon atoms, or a 5- to 6-membered unsaturated or saturated heterocyclic group having up to 3 hetero atoms from the series consisting of S, N and O, or represent a group of the formula —NR³R⁴ or —NR⁵SO₂R⁶, wherein R³, R⁴ and R⁵ are identical or different and denote hydrogen or straight-chain or branched alkyl having up to 4 carbon atoms or phenyl, R⁶ denotes straight-chain or branched alkyl having up to 4 carbon atoms, benzyl or phenyl, which is optionally substituted by straight-chain or branched alkyl having up to 4 carbon atoms, L represents a bond, or represents a group of the formula

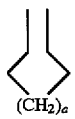

wherein

R⁷ denotes hydrogen, hydroxyl, methoxy or hydrogen,

R⁸ denotes hydrogen, hydroxyl, halogen, straight-chain or branched alkenyl or alkoxy having in each case up to 8 carbon atoms or cycloalkyl or cycloalkenyl having in each case 3 to 14 carbon atoms, or denotes straight-chain or branched alkyl having up to 8 carbon atoms, which is optionally substituted by cycloalkyl having 3 to 8 carbon atoms, phenyl or tetrahydropyranyl, which in their turn can be substituted by halogen, or denotes a group of the formula —CH₂SIR⁹R¹⁰R¹¹ or an indanyl group, wherein R⁹, R¹⁰ and R¹¹ are identical or different and denote straight-chain or branched alkyl having up to 4 carbon atoms or R⁷ and R⁸ together with the carbon atom form a saturated carbocyclic ring having 5 to 7 carbon atoms, which is optionally substituted up to mice in an identical or different manner by straight-chain or branched alkyl having up to 4 carbon atoms, or R⁷ and R⁸ together form a group of the formula =O or a double bond group of the formula $$\underset{(CH_2)_a}{\bigwedge}$$

wherein a denotes the number 2, 3, 4, 5 or 6, and salts thereof.

2. Oxy-phenyl-(phenyl)glycinolamide with heterocyclic substituents, according to claim 1, in which A represents naphthyl or represents a group of the formula

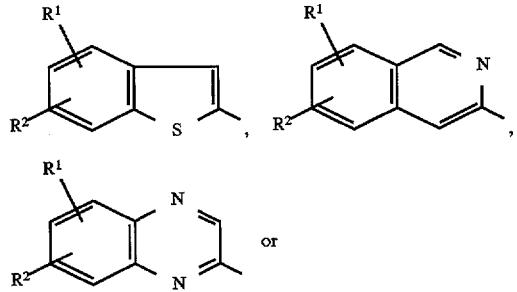

wherin

R¹ and R² are identical or different and denote hydrogen, fluorine, chlorine, bromine, hydroxyl or straight-chain or branched alkoxy having up to 3 carbon atoms, D and E are identical or different and represent hydrogen, cyclopropyl, cyclopentyl, cyclohexyl, azido, hydroxyl, fluorine, chlorine, bromine, straight-chain or branched alkyl, alkoxy, or alkenyl having in each case up to 5 carbon atoms, pyrryl or imidazolyl, or represent a group of the formula —NR³R⁴ or —NR⁵—SO₂—R⁶, wherein R³, R⁴ and R⁵ are identical or different and denote hydrogen, straight-chain or branched alkyl having up to 3 carbon atoms or phenyl, R⁶ denotes straight-chain or branched alkyl having up to 3 carbon atoms, benzyl or phenyl, which is optionally substituted by straight-chain or branched alkyl having up to 3 carbon atoms, L represents a bond, or represents a group of the formula

wherein

R⁷ denotes hydrogen, hydroxyl, methoxy, fluorine, chlorine or bromine,

R⁸ denotes hydrogen, hydroxyl, halogen, straight-chain or branched alkenyl or alkoxy having in each case up to 7 carbon atoms, cyclopentyl, cyclohexyl, cycloheptyl, cyclooctyl, cyclononyl, cyclodecyl, cycloundecyl, cyclododecyl or cyclohexenyl, or denotes straight-chain or branched alkyl having up to 7 carbon atoms, which is optionally substituted by cyclopentyl, cyclohexyl, cycloheptyl, cyclooctyl, phenyl or tetrahydropyranyl, which in their turn can be substituted by fluorine, chlorine or bromine, or denotes a group of the formula CH₂—SiR⁹R¹⁰R¹¹ or an indanyl group, wherein R⁹, R¹⁰ and R¹¹ are identical or different and denote straight-chain or branched alkyl having up to 3 carbon atoms, or R¹³ and R¹⁴ together with the carbon atom form a cyclopentyl, cyclohexyl or cycloheptyl ring which are optionally substituted up to twice by methyl, or R⁷ and R⁸ together form a group of the formula =O or a double bond group of the formula

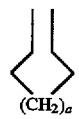

wherein a denotes the number 2, 3 or 4, and salts thereof.

3. Oxy-phenyl(phenyl)glycinolamides with heterocyclic substituents, according to claim 1, in which A represents naphthyl or represents a group of the formula

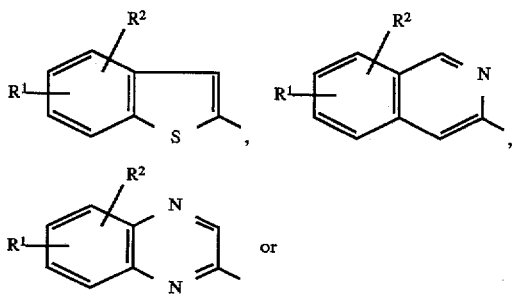

wherein

R¹ and R² are identical or different and denote hydrogen, fluorine, chlorine, bromine, hydroxyl or methoxy, D and E are identical or different and represent hydrogen, cyclopropyl, cyclopentyl, cyclohexyl, azido, hydroxyl, fluorine, chlorine, bromine, straight-chain or branched alkyl, alkoxy or alkenyl having in each case up to 5 carbon atoms, pyrryl or imidazolyl, or represent a group of the formula —NR⁵—SO₂—R⁶, wherein R⁵ denotes hydrogen or methyl, R⁶ denotes straight-chain or branched alkyl having up to 3 carbon atoms, benzyl or phenyl, which is optionally substituted by methyl or ethyl, L represents a bond, or represents a group of the formula

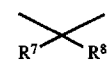

wherein

R⁷ denotes hydrogen, hydroxyl, fluorine or methoxy,

R⁸ denotes hydrogen, hydroxyl, straight-chain or branched alkenyl or alkoxy having in each case up to 6 carbon atoms, cyclopentyl, cyclohexyl, cycloheptyl, cyclooctyl, cyclononyl, cyclodecyl, cycloundecyl, cyclododecyl or cyclohexenyl, or denotes straight-chain or branched alkyl having up to 6 carbon atoms, which is optionally substituted by cyclopentyl, cyclohexyl, cycloheptyl, phenyl or tetrahydropyranyl, which in their turn can be substituted by fluorine, chlorine or bromine, or denotes a group of the formula CH₂Si(R⁹R¹⁰R¹¹) or an indanyl group, wherein R⁹, R¹⁰ and R¹¹ denote methyl, or R⁷ and R⁸ together with the carbon atom form a cyclopentyl, cyclohexyl or cycloheptyl ring, which are optionally substituted up to twice by methyl, or R⁷ and R⁸ together denote a group of the formula =O or a double bond group of the formula

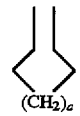

wherein a denotes the number 2, 3 or 4, and salts thereof.

4. A composition for the treatment of atherosclerosis comprising an amount effective therefor of a compound or salt thereof according to claim 1 and a pharmacologically acceptable diluent.

5. The method of treating atherosclerosis in a patient in need thereof which comprises administering to such patient an amount effective therefor of a compound or salt thereof according to claim 1.

* * * * *